United States Patent [19]

Taylor

[11] Patent Number: 5,451,787
[45] Date of Patent: * Sep. 19, 1995

[54] HAZARDOUS AIR POLLUTANTS MONITOR

[75] Inventor: Lyle H. Taylor, Murraysville, Pa.

[73] Assignee: Westinghouse Electric Corporation, Pittsburgh, Pa.

[*] Notice: The portion of the term of this patent subsequent to Dec. 13, 2011 has been disclaimed.

[21] Appl. No.: 321,228

[22] Filed: Oct. 11, 1994

Related U.S. Application Data

[63] Continuation-in-part of Ser. No. 58,191, May 4, 1993, Pat. No. 5,373,160.

[51] Int. Cl.[6] .................... G01N 21/17; G01N 21/35
[52] U.S. Cl. ........................ 250/338.5; 250/339.13; 250/343
[58] Field of Search .............. 250/338.5, 339.13, 343

[56] References Cited

U.S. PATENT DOCUMENTS

| | | | |
|---|---|---|---|
| 4,496,839 | 1/1985 | Bernstein et al. | 250/341.6 |
| 4,602,342 | 7/1985 | Gottlieb et al. | 364/498 |
| 5,076,699 | 12/1991 | Ryan et al. | 356/437 |
| 5,202,570 | 4/1993 | Tanaka et al. | 250/575 |
| 5,373,160 | 12/1994 | Taylor | 250/338.5 |

Primary Examiner—Carolyn E. Fields
Assistant Examiner—Edward J. Glick

[57] ABSTRACT

Gases such as pollutants are discerned in a sample, preferably using a laser to emit an infrared light beam along a sight path for illuminating the gases. The beam is directed along the sight path and collects light from the gases. An optical tunable filter selects a particular optical wavelength or band, and the filtered wavelength is focused on a detector coupled to an analyzer. The analyzer can include a processor that can pulse the laser or coordinate collection of data from sample gases and from a reference cell containing known gases, e.g., using an optical chopper wheel. The processor analyzes the light levels as a function of wavelength to discriminate for the presence of selected gases by determining a characteristic pattern of light absorption and light emission by the gases. The tunable filter has an acousto-optical crystal of $Tl_3AsSe_3$, in which an RF acoustic wave is generated for varying diffraction of light by the filter, thereby selecting a wavelength. A nonlinear output crystal can in inserted controllably to selectively generate harmonics for increasing wavelength coverage, and can also be $Tl_3AsSe_3$. A broad band infrared illumination source can be used. When the infrared excitation beam is off, the filter acts on infrared emissions of the gases. Sensitivity to narrow emission lines is increased by modulating the RF drive to the tunable filter, producing derivatives of the spectra.

23 Claims, 2 Drawing Sheets

HAZARDOUS AIR POLLUTANTS MONITOR

CROSS REFERENCE TO RELATED APPLICATION

This application is a continuation-in-part of U.S. patent application Ser. No. 08/058,191, filed May 4, 1993, now U.S. Pat. No. 5,373,160.

BACKGROUND OF THE INVENTION

1. Field of the Invention

The invention relates to methods and apparatus for monitoring air quality, in particular for identification of airborne molecules and concentration measurements, for example the emissions of a particular stack of a manufacturing plant. A combination of infrared absorption and emission spectroscopy is effected by an automatically controlled spectroscopic device.

A pulsed or continuous wave $CO_2$ laser can be directed selectively through or around a doubler crystal for operation in different frequency bands. An electroacoustic tunable filter and detector arrangement discriminates for absorption and emission at particular frequencies characteristic of pollutant gases, and a computer decodes the timing and absorption/emission information as a function of optical wavelength and distance. The computer preferably also generates and records a profile of gas concentrations along the sight path, including the concentrations of hazardous pollutant gases.

2. Prior Art

Infrared spectroscopy is a known method for assessing concentrations of gases in samples. Systems that use a laser and an acousto-optic tunable filter are disclosed, for example, in U.S. Pat. Nos. 4,490,845—Steinbruegge et al; 4,622,845—Ryan et al; and 4,652,756—Ryan et al. The technique generally involves passing an infrared band laser beam from a source to a detector, across the flowpath of gases in a stack. Reflectors can be used to pass the beam across the stack more than once, thus increasing the extent to which the beam is affected by the sample of gases in the stack. Typically, the path of the beam is "closed," i.e., the light passes from the source, through the gas, to the detector. Gases in the stack absorb the illuminating radiation selectively at specific frequencies due to the molecular and atomic structure of the gas molecules. The detector discriminates for known patterns of absorption, i.e., absorption at certain wavelengths and not at other wavelengths.

Gas also may emit radiation at specific frequencies due to fluorescence effects following the application of sufficient excitation energy or by thermal excitation which produces blackbody radiation. Fluorescence effects are a form of reflectance. Normally, fluorescence is very low in power compared to the illuminating energy. Thus fluorescence is difficult to detect in a closed path arrangement during illumination, or in a closed path arrangement wherein the detector determines absorption as a function of wavelength in the range of illumination. Fluorescence measurements also typically are conducted at close range, to enable application of sufficient excitation energy to produce a detectable response. By analyzing the energy received as a function of frequency or wavelength, it is possible to detect the presence of particular molecules, and to assess the concentration of these molecules in the stack gases. According to the patents to Ryan et al, stack monitoring is done repetitively in an automated manner using a computer controller and analyzer for controlling a tunable filter at the receiver.

Monitoring stack gases requires a detection arrangement that is fixed and applicable only to measure the instantaneous concentration(s) of gas(es) in the stack. In conjunction with a flow measurement technique, this information can be converted into a gas volume figure that may be meaningful with respect to any air pollution at large. It would be advantageous to facilitate fast and automated measurements across open air where needed, and to provide a system with the versatility needed to discriminate for a wide variety of gases.

In general, there are five open path remote sensing techniques applicable to assessment of gas concentrations in the air. These are fluorescence, differential optical absorption spectroscopy, tunable diode laser absorption spectroscopy, differential absorption lidar spectroscopy, and Fourier transform infrared spectroscopy. These are each methods for measuring the wavelength-specific behavior of the gas molecules such that characteristic patterns that represent particular gases can be identified in the data.

The fluorescence technique measures the light intensity emitted by specific gases at characteristic wavelengths. The light is emitted when electrons in the gas molecules return to a lower energy state after the molecules have been excited, typically by radiation from a high intensity light source. Fluorescence measurement is restricted to measurements in the ultraviolet, where OH radicals and $SO_2$ can be effectively discriminated by characteristic spectroscopic signatures. However, expensive equipment is required and the equipment is designed to measure only for specific pollutants. The technique lacks versatility and is operable only with respect to a sample that is very close to the illumination source and the detector.

Differential optical absorption spectroscopy involves measuring the differential intensities between absorption peaks and valleys versus wavelength in the ultraviolet-to-visible regions. The light source is usually a high intensity lamp and the maximum path length is around 800 m. This method has good specificity for discriminating among gases, and is the only method that effectively measures $NO_3$ radicals. Equipment for making the measurements is readily available, for example as embodied in the OPSIS system, installed at various locations in Europe. However, because the system does not encompass the mid-to-far infrared spectral band, it is ineffective for discriminating most molecular hydrocarbon concentrations, which unfortunately include many pollutants that it would be desirable to detect.

Mid-IR tunable diode lasers are available for tunable diode laser absorption spectroscopy. A tunable light source, as opposed to a wide band light source, can simplify the equipment required for light absorption spectroscopy because the sample can be illuminated at the wavelengths of interest, and the absorption of the light at these frequencies can be examined. The tunable diode approach has high time resolution, excellent specificity, high sensitivity for $NO_2$, and also measures $HNO_3$, $NH_3$, $HCHO$ and $H_2O_2$ at trace levels. It detects pollutants that other techniques cannot, and/or has a higher sensitivity due to precise control of illumination wavelength. However, laser diodes of sufficient power do not exist for the far-IR region where most hydrocarbon pollutants absorb. In the wavelengths where tunable diode lasers operate, power constraints of the source and sensitivity limitations of detectors limit atmospheric absorption measurements to a path length of about 300 m.

Instead of using fixed reflection targets, differential absorption lidar spectroscopy uses atmospheric backscatter of tunable pulsed lasers. This technique measures absorption and has been most successful in the ultraviolet and visible regions, where molecular scattering is prevalent. In the IR band, aerosols must provide the scattering. This technique has the advantage that range-resolved profiles over a substantial distance (e.g., 3 km) can be developed, i.e., the concentrations of detected gases as a function of distance from the source/detector. The present invention may also use a pulsed laser with a ranging capability, which enables localization and volume measurements of pollution clouds. The invention, however, is arranged to operate in the mid-to-far infrared, and uses a tunable receiver.

Fourier transform infrared spectroscopy involves interferometry. A beam from a high intensity lamp is propagated through the atmosphere and split into two beams at the receiver. One beam is directed to a fixed mirror and the other beam to a moving mirror. The two beams are recombined to form an interferogram from which the absorption spectra is obtained. This technique is useful in the two IR atmospheric transmission windows where many toxic pollutant chemicals absorb, i.e., 3.3 to 4.2 $\mu$m and 8.3 to 13.3 $\mu$m. The method is good for relatively high pollutant concentrations, but it is limited in that the sensitivity for most pollutants is not sufficient for ambient monitoring in moderately polluted or unpolluted areas, where it may be desirable to detect and measure for traces. Moreover, the range is limited to about 500 m.

Unless one desires to measure only for the specific type of gas and concentration range, and perhaps at a specific location for which the foregoing monitoring systems are respectively designed, more than one of them is needed to avoid the drawbacks of power, frequency and sensitivity limitations of each. It would be possible to combine all the foregoing types of monitors in one system, to provide a measurement and detection system that enjoyed the advantages of the respective techniques. This would be prohibitively expensive and complex.

According to the present invention, infrared spectroscopy techniques are applied to a directable sighting device having an automated tunable filter detector arrangement and a multi-band or wide band source having means for selectively directing an illuminating beam through a nonlinear crystal to produce harmonics. The tunable filter is preferably an acousto-optical tunable diffractor, e.g., comprising at least one crystal of thallium arsenic selenide ($Tl_3AsSe_3$) or any other acousto-optic material. This crystal is operable as a tunable diffractor by varying the frequency of a modulating acoustic wave passed through the crystal by application of a radio frequency modulating field.

U.S. Pat. No. 3,805,196—Feichtner et al discloses how to make and use a thallium arsenic selenide or "TAS" crystal as a controllable diffractor. The acoustic wave generated in the crystal produces alternating compression and rarefaction fronts, which have different indices of refraction. The wave fronts form a diffraction grating that spreads the spectrum of light passed therethrough, and diverts the received beam as a function of wavelength. The angle of refraction of the grating can be adjusted with the frequency of the acoustic wave, and the amount of light diffracted increases with the intensity of the acoustic wave. Therefore, by varying the acoustic frequency the crystal is tuned such that a particular wavelength can be directed on a detector. Furthermore, the angular shift of the diffracted beam can be mostly compensated by creating a wedge at either the input or output optical face of the acousto-optic tunable filter, with the result that the diffracted beam always appears at the same angle to the detector irrespective of the acoustic frequency. The output of the detector is digitized and stored to develop absorption information as a function of optical wavelength. A computer then determines the concentrations of gases along the sight path from their characteristic absorption spectra.

U.S. Pat. No. 4,505,550—Steinbruegge discloses an acousto-optic tunable filter in infrared bandwidths, useful for imaging equipment. U.S. Pat. Nos. 4,575,186—Gottlieb et al, and 4,705,362—Ryan et al disclose variations including, for example, a plurality of crystal arrangements for operating in different bands to enlarge the bandwidth of the filter as a whole. Each of the foregoing patents is hereby incorporated as if set forth in full.

SUMMARY OF THE INVENTION

It is an object of the invention to provide an open path infrared spectrometer arrangement that is highly specific, versatile and inexpensive.

It is also an object of the invention to provide an automated spectrographic analyzer that can measure gas concentrations rapidly, in situ, avoiding the loss of radicals.

It is a further object of the invention to employ acousto-optical crystals for controllable selection of illumination at basic and harmonic illumination wavelengths, and to selectively filter light reflections, absorptions and emissions of gases to identify particular molecules by detecting spectral patterns characteristic of the molecules.

It is another object of the invention to probe regions that are not accessible to point monitors, and to automatically control illumination and measurements for completing a scan for hazardous pollutants in a short time.

These and other objects are accomplished by selectively discerning gases such as pollutants along an open air path, including emitting an infrared light beam along a sight path through the air, preferably using a laser, thereby illuminating gases along the sight path. A viewing means is directed along the same sight path, and collects light from the gases in the air, the combination of the laser and viewing means permitting redirection of the sight path. The sight path can be directed through gases flowing through a stack, e.g., laterally or longitudinally. An optical tunable filter is coupled to the viewing means for selecting a particular optical wavelength or band, and focusing the filtered wavelength on a detector. A processor is coupled to the detector output and controls the laser and otherwise operates to coordinate collection of the data. The processor analyzes the light levels as a function of wavelength to discriminate for the presence of selected gases by determining a characteristic pattern of light absorption and light emission by the gases. The tunable filter has an acousto-optical tunable filter with a crystal of $Tl_3AsSe_3$ or another acousto-optical material. An alternating electric field is applied to a transducer bonded to the crystal to set up an acoustic wave for varying the angle at which light is diffracted through the filter, thus selecting a wavelength. The electric field can be changed rapidly in frequency, to advance the detector arrangement from one wavelength to another, and collecting spectrographic information. A second crystal preferably is selectable by the controller, to generate harmonics as an alternate source of laser illumination in a different optical band. The second crystal, namely the output crystal, can also be Tl$_3$AsSe$_3$ or another nonlinear optical material. The output crystal is disposed between the laser and the sight path, and produces at least one harmonic wavelength, whereby the laser is selectively operable to illuminate the gases along the sight path at a plurality of illumination frequencies.

BRIEF DESCRIPTION OF THE DRAWINGS

The invention is illustrated with respect to particular embodiments that are exemplary rather than limiting. Reference should be made to the appended claims rather than the specific embodiments disclosed as examples, to assess the scope of the invention in which exclusive rights are claimed. In the drawings.

DETAILED DESCRIPTION OF THE PREFERRED EMBODIMENTS

The invention applies acousto-optic tunable filter technology and tunable laser capability in the mid to far infrared (IR) band, to provide an instrument for optical remote measurement of concentrations of atmospheric gases. A multitude of hazardous air pollutants, including pollutants specified in the 1990 Clean Air Act Amendments, can be distinguished in this manner, and furthermore, localized concentrations can be measured as to size, concentration and component molecules. In the mid to far IR, most hydrocarbons can be identified by their absorption spectra, thereby complementing measurements in ultraviolet (UV) and visible bands, where homonuclear and light molecules have their main absorption spectra.

The measurement according to the invention is very fast. For example, 2 minutes is sufficient to collect enough information as to absorption/reflectivity of the gases along the sight path to distinguish 120 particular gases. By taking wavelength specific measurements as a function of time, pollutant gases are discernable and their concentrations can be quantified.

Figure 1:
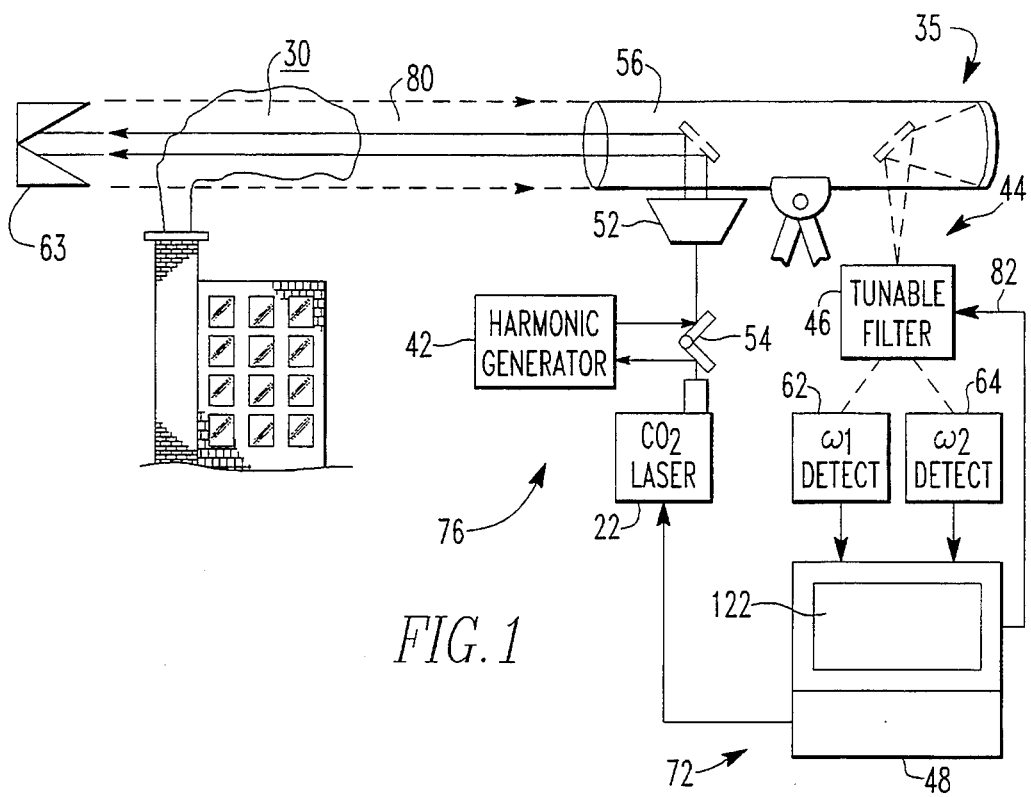
FIG. 1 is an overall block diagram showing a first embodiment of the apparatus according to the invention.
Figure 3:
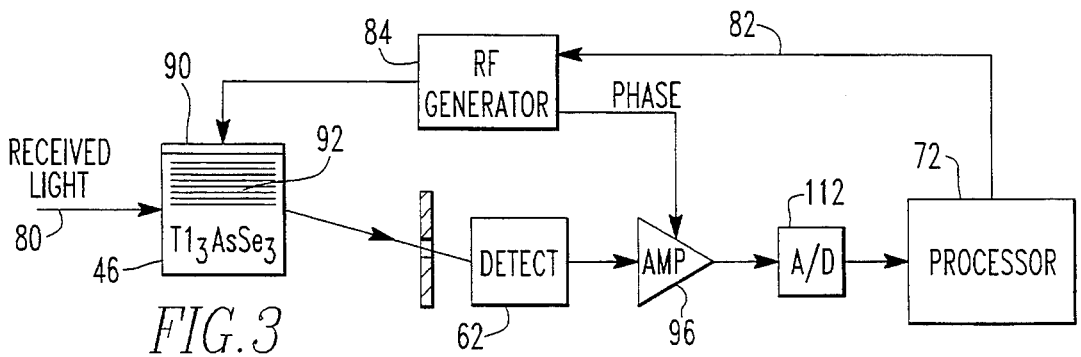
FIG. 3 is a schematic illustration showing application of the tunable optical filter.

FIG. 1 illustrates the elements of a preferred embodiment. The monitoring system 35 measures atmospheric absorption by hazardous air pollutants 30 over open paths. An infrared source such as a 1 W continuous wave ("cw") or 15 mJ pulsed CO$_2$ laser 22 can be operated at a pulsed frequency of 300 Hz, at an optical wavelength tunable from 9.2 to 10.8 $\mu$m. The intensities of light returning along the sight path from hazardous air pollutants, e.g., in a band from 9.2 to 10.8 $\mu$m, are measured and digitized, developing spectrographic information which is analyzed by the processor/controller 48, including a numerical processor 72 as shown in FIGS. 1 and 3, to assess the presence of selected gases.

An optional enhancement is preferably employed selectively to enlarge the optical illumination bandwidth. A harmonic generator or doubler 42 increases the CO$_2$ laser output frequencies into the 4.6 to 5.4 $\mu$m spectral range. The doubler 42 can be inserted automatically into the output illumination path for spectral analysis of absorption/reflectivity in this band. For efficient operation of the harmonic generator, the CO$_2$ laser preferably is pulsed.

As shown in FIG. 1, the hazardous air pollutants monitor 35 according to the invention comprises four main components. These are an infrared source such as CO$_2$ laser 22, a nonlinear crystal or doubler 42, a receiver 44 including an acousto-optic tunable filter 46, and a computer 48 for analyzing collected data and for controlling system operation. Preferably, these elements are coupled optically using a beam expander 52, a gimballed turning mirror 54, and a directable optical viewing means 56. The laser 22 and beam expander 52 direct illumination along the beam path 80, and are mounted commonly with the viewing means 56 to illuminate and view along a common path between the measuring system 35 and a reflector 63 that can be located diametrically opposite in a stack. The viewing means 56 focuses light from the sample on at least one, and preferably two detectors 62, 64. The detectors can include a 5–14 $\mu$m detector 62 and a 2–5 $\mu$m detector 64, which are operated selectively in conjunction with control of the illumination wavelength selected by the laser output means, generally designated 76. The detectors 62, 64 are controllably coupled to an electronic controller, preferably provided as a function of computer 48, that sequences system operation and analyzes the collected data to decode the measurement results.

The computer or other controller 48 cycles through a range of wavelengths, collecting spectrographic information regarding the absorption or reflection of light returning from the gas 30 and/or the topographic target. The computer then correlates the absorption lines detected in the spectrograph with particular gas compositions in the sample, and logs or reports the results.

The receiver portion 44 can be line-tuned for specific optical wavelengths, and the pulse/measurement operation can be accomplished at a high repetition rate (e.g., 300 Hz) for quick measurements sufficient to identify the absorption signatures of a number of different gases in the spectrographic data collected. The wavelength specific data is collected at the high resolution of the laser bandwidth ($\approx 0.01$ cm$^{-1}$).

The laser output means 76 and the viewing means coupled to the receiver 44 are mounted commonly. Accordingly, the measurement device 35 readily can be redirected at a new target, in real time, simply by redirecting the output beam. Thus, where appropriate alternative areas can be quickly monitored by undertaking measurements along several beam paths. Similarly, the beam path can be changed quickly to locate pollution sources or concentrations wherever they may occur or be suspected.

Figure 2:
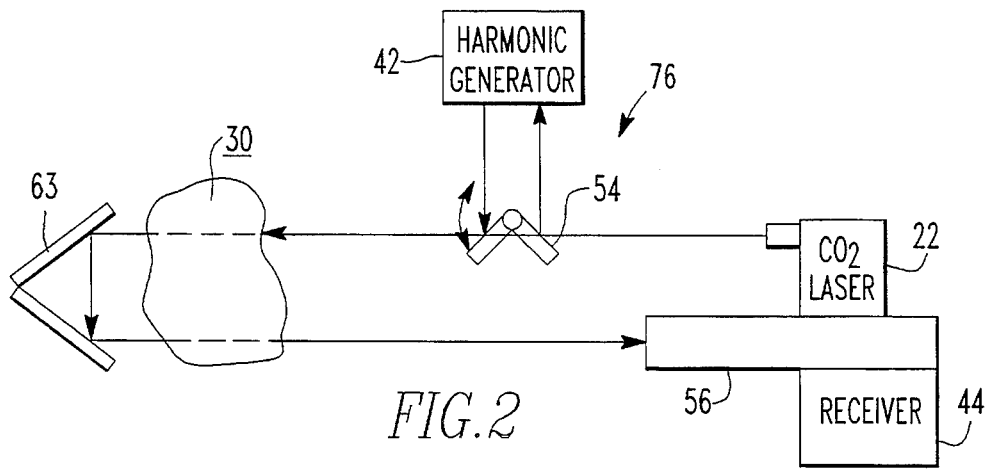
FIG. 2 is a schematic diagram showing the functional control and measurement arrangements of the components.

The CO$_2$ laser frequency preferably can be doubled via a nonlinear crystal 42 as shown in FIG. 2. The crystal can be a Tl$_3$AsSe$_3$ nonlinear crystal, as discussed in the infrared imaging patent disclosures discussed in the prior art section, above, which patents are hereby incorporated in their entireties. Preferably, the gimballed mirror 54 allows the laser beam to be directed through or around the doubler crystal 42, under control of the processor 48. Preferably, the apparatus 35 is controlled to analyze for absorption characteristics in a band centered at the basic laser wavelength, and then at the shorter harmonic wavelengths provided by the doubler crystal 42. An advantage of the shorter wavelengths provided by this option is that some gases (e.g., CO, NO, HBr, HI, OCS, and $N_2$) absorb in the 4.6 to 5.4 $\mu$m range but not in the 9.2 to 10.8 $\mu$m range. According to the invention, electronically activated two-position turning mirrors 54 direct the $CO_2$ laser beam through the crystal 42 for short wavelength operation and around the crystal 42 for long wavelength operation. The mirrors 54 can be operated by a control signal from the processor 48, which triggers operation of a solenoid or the like (not shown) to divert the mirrors 54 from the beam path or to insert the mirrors into the beam path and thereby redirect the beam through or around the doubler crystal 42 as required for that phase of system operation.

The viewing means 56 collects and concentrates returning light on the acousto-optical filter 46. The filter 46 includes an acousto-optic $Tl_3AsSe_3$ material and an RF generator or oscillator 84, shown in FIG. 3. The oscillator 84 is controlled by the processor 48 for directing an acoustic wave through the crystal at a selected radio frequency, coupled to the crystal via transducer 90, bonded thereto. The acoustic wave fronts 92 form a diffraction grating in the crystal 46. By varying the acoustic frequency, the diffraction effects of the crystal 46 are changed, selectively varying the wavelength band applied to the detector 62 or 64, which can have a narrow slot input as shown in FIG. 3. The crystal of the tunable filter is used in this manner to direct a selected wavelength portion of the beam to the proper detector 62, 64. Two transducers 90 can be bonded to orthogonal faces of the crystal, for diffracting the incoming infrared radiation to the two detectors 62, 64.

The acousto-optical filter 46 has two key functions in the receiver 44. During absorption measurements, the narrow filter passband greatly increases the signal-to-noise ratio of the system by restricting the radiation applied to the detector 62, 64 from the atmosphere to a narrow spectral range, e.g., 2–10 $cm^{-1}$, around the absorption line which is then selected. The frequency of the acoustic beam determines the center wavelength of the optical passband and is electronically controlled to center the passband around the laser wavelength. During emission measurements, direct spectroscopy or derivative spectroscopy can be applied in which the acousto-optical filter 46 is tuned to between 3.5 and 14 $\mu$m. Sharp laser lines or emission lines are measured by modulating the acoustic frequency at a fixed frequency, e.g., 1 KHz, to sinusoidally shift the passband of the acousto-optical filter. The modulation does not affect radiation which has a relatively constant intensity over the acousto-optical filter passband, but modulates the intensity from emission lines or laser lines much narrower than the passband. A phase locked amplifier 96 tuned to the modulation frequency separates the modulated signal from the background. For narrow lines in a blackbody background at the same temperature, this approach gives a signal-to-background ratio of 11 at 10.6 $\mu$m, increasing to 43 at 5 $\mu$m.

The measurement system 35 can operate repetitively to sequence through a series of measurements intended to identify particular pollutant gases by their absorption spectra. Key emission lines can be monitored during those scheduled times when more extensive measurements are not being taken. If preset thresholds are exceeded (i.e., if the processor detects in the data a predetermined concentration of one or more pollutant gases), the system can be programmed to switch automatically to detailed measurements, selection of certain bands or wavelengths for more extensive analysis and/or selection of derivative spectroscopy measurements to supplement absorption measurements. This dual emission-/absorption monitoring under automatic control of the processor/controller 48 reduces the volume of information that needs to be processed routinely, as compared to a system that collects all possible data all the time.

The processor 48 controls and sequences operations, and analyzes collected data for characteristic spectral lines. The processor 48 can comprise a commercial personal computer having data acquisition means 112 which sample and digitize the detector output levels, and one or more outputs 82 for controlling the tunable filter 46 and gimballed mirror arrangement 54. The processor 48 determines concentrations from the measured spectroscopic data. The processor 48 can include a numeric processor for analyzing the data and an electronic controller which may be a separate processor operable to control the laser, the acousto-optical tunable filter, and the directional optics. Alternatively, the numeric and control functions can be embodied in one computer 48.

Preferably, processed information from the data is displayed on a screen monitor 122. The raw and/or processed data can be stored on disc for later analysis, printed, reported remotely, used to trigger alarms, etc.

Whereas the measurement system as a whole can be oriented in any direction through the open air, the invention is able to probe selected regions. The measurement system 35 can be directed manually at desired pollution sources or can be automatically positionable, e.g., by motor drives (not shown) under control of the processor 48. In this manner the processor 48 can sequence through measurements of a number of preprogrammed angles, and in each case measure and log information on the gases detected. The orientation of the measurement beam 80 can be encoded and stored with the spectral data, to associate the specific measurements with specific sites.

The processor 48 can proceed rapidly through a number of particular wavelength and illumination (absorption), excitation (fluorescence) and/or thermal emission measurement steps. Thus it is possible to determine concentrations of a large number of gases in minutes, rather than hours. The gases are sampled in-situ, thus avoiding losses of radicals that might occur from testing relying on sample collection and later testing.

Path-averaged measurements are available in this manner for accurate monitoring. The system is further capable of responding rapidly to changing situations, e.g., the system can be arranged to hunt for pollution sources or to take detailed measurements relating to a localized gas concentration such as the plume of a single pollution source.

A tunable diode form of laser measurement according to the invention may become viable with the development of more powerful diode lasers, but is presently not preferred as being too restricted in power and wavelength coverage to be effective. Thus a controllably pulsed or cw $CO_2$ laser is employed in the exemplary embodiment shown.

The differential absorption lidar approach is applicable to any pulsed laser range finding arrangement, and preferably is employed according to the invention as an analytical technique. Differential optical absorption spectroscopy normally encompasses the UV to near-IR regions, whereas Fourier transform infrared spectroscopy, like the present invention, is useful in the mid-to-far IR regions. Thus, a complete analysis system according to the invention employs differential optical absorption and the monitor discussed above, to encompass a full range of wavelengths of interest. It is also of course possible to restrict the function of the arrangement, for example, embodying the apparatus only to take path averaged absorption measurements or the like, for applications in which the full range of measurements are not needed.

Although the monitor of the invention does not presently cover the broad 3-13 $\mu$m absorption spectral range of Fourier transform infrared spectroscopy, the invention does cover the most important spectral ranges, i.e., those ranges in which most hazardous pollutants absorb. In any event, the monitor of the invention is substantially faster and less labor intensive than present techniques for measuring the concentrations of several gases.

In principle, a Fourier transform infrared spectrum can be collected in less then 10 ms. However, to achieve good sensitivity it is necessary to integrate the collected data over many measurements. A total time of about four minutes is thus used to integrate over 170 samples. By comparison the automated monitor according to the invention can integrate over 170 samples per gas in about 1 second, thus completing the analysis for 240 gases in the same four minutes.

In absorption measurements at short wavelengths, the invention has an operating distance and sensitivity comparable to a Fourier transform technique. However, the resolution of the monitor of the invention can be made narrower than with a Fourier transform technique. At the longer wavelengths containing the characteristic absorption lines of most hazardous pollutants, the $CO_{12}$ pulsed laser according to the invention is over 100 times brighter than the brightest incoherent sources, thereby making the invention much more sensitive than a Fourier transform analyzer. The monitor of the invention is 10 to 40 times more sensitive in emission measurements and encompasses the same wavelength range as a Fourier transform analyzer for this measurement application. The invention thus has a major advantage in providing unattended automated operation and in assessing and monitoring pollution sources.

Figure 4:
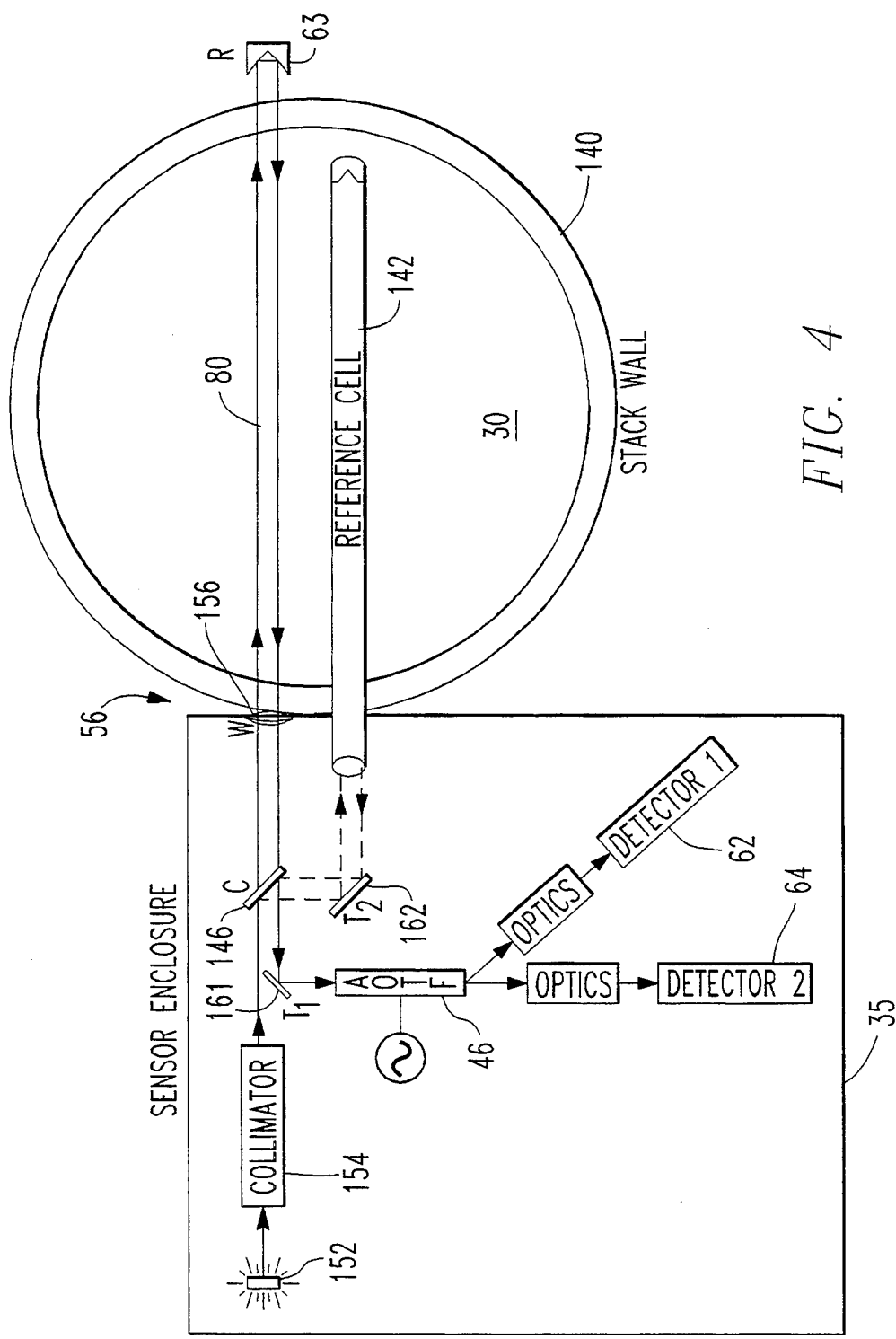
FIG. 4 is a schematic block diagram showing application of the invention to monitoring through a cross section of stack gases.

FIG. 4 illustrates further aspects of the invention, and in particular concerns the application of the invention to an open path measurement across the gases passing through a stack 140. Preferably, a reference cell 142 is provided to enable comparison between spectral data collected from the stack gases in the open path, and reference gases contained in known concentrations in a closed container. The reference cell 142, for example, can contain minority gas concentrations in one atmosphere of nitrogen, providing means for calibration and wavelength checks, plus baseline determination from the nitrogen. These embodiments permit differential measurements to determine stack gas concentrations, for example with the stack gases and the reference cell gases being measured alternately. Providing such a reference cell reduces any effect from long term drift due to component aging, temperature variation and the like.

In FIG. 4, the AOTF is used to measure for gases in the stack and in a reference cell. A rotating optical chopper 146 is used for making alternate measurements of the stack gases and the reference cell gases.

The illumination source is shown generally in FIG. 4 to include an infrared source 152 and a collimator 154. These components can be provided by using an infrared laser such as a $CO_2$ laser as in the foregoig embodiment, which produces a controllable coherent collimated beam having a very small bandwidth. Alternatively, a wide band source together with collimating optics can be used. One possible wide band source is a Nernst glower such as a 1.5 mm diameter rod, 5 mm long, comprising compressed zirconium and yttrium oxides, with platinum connectors coupled to a power supply for operating the glower at about 2100° K.

The beam is directed outwardly into the stack gases through a ZnSe window 156, traverses the stack gases and is redirected back through the same ZnSe window by a retroreflector 63. The illumination source and retroreflector can be disposed along the stack and arranged to view through the stack wall, or alternatively the arrangement can monitor at the discharge end of the stack or at the inlet thereto. Air curtain arrangements (not shown) can be used to minimize the accumulation of dust or soot on window 156 and retroreflector 63, the latter essentially comprising two mirrors arranged at 45° to the beam axis.

The chopper 146 either passes the beam to the open path gases 30 or reflects the beam to turning mirror 162 and reference cell 142, effecting a time division multiplexing arrangement. Cell 142 likewise has a retroreflector at its end remote from the source, and returns the beam along the same beam path as the beam returning along the open path from the stack.

The returning beam that either passes back from open path gases 30 through chopper 146 or is intercepted from the reference cell 142 and turning mirror 162 by the chopper, are directed to the input aperture of AOTF 46. This can be accomplished using another turning mirror 161 as shown. The AOTF is coupled to an acoustic driving frequency that controllably diffracts the beam as discussed above, to select a small spectral slice of the input spectrum, for example with a spectral width of about 2 cm$^{-1}$, at a center wavelength determined by the acoustic driving frequency. The diffracted portion of the beam is directed to a first detector 62, which as discussed above can have two detector elements, adapted for different wavelength ranges. The remaining and major portion of the input beam that lies outside the narrow spectrum to which the AOTF is tuned, goes straight through along the main axis into matching optics for a second detector 64. This optional second detector is included, for example, to measure the total radiation loss, which is useful to assess approximate particle size because scattering efficiency depends in part on the ratio of wavelength to particle diameter.

The embodiment of FIG. 4 can have a 50% duty cycle, alternately measuring the response of the stack gases 30 and the reference cell 142. The acoustic frequency and power are substantially the same for the beams directed through the open path stack gases and through the reference cell 142. Thus the signals from detectors 62, 64 can be compared by storing the signals (or a preprocessed version of the signals) for one of open path gases 30 and reference cell 142 gases, and comparing them to the other.

Chopper wheel 146 can have, for example, four mirrored segments and four open segments around its circumference, and is rotated at 103 revolutions per second, producing ac signals at the detector at the rate of 412 Hz and permitting filtering out of 60 Hz ac power line noise by bandpassing.

Collimated radiation through an open segment passes through window 156, through the open path gases and is directed back. To improve sensitivity, it is possible to direct the beam several times back and forth between retroreflectors on opposite sides (only one being shown) and thereby increase the exposure of the beam to gases in the open path sample, in any event the beam being directed back along the same path to be intercepted by turning mirror 161 and directed to the AOTF. The magnitude of the successive measurements can be compared by ratios to eliminate any baseline shift.

The reference cell 142 can be a 13 cm diameter, 59 cm long glass-bodied long-path cell with an aluminum supporting structure. A ZnSe window and opposite end retroreflectors can provide multiple passes through the reference gases, for example to obtain a multiple pass total path of 22 m. Preferably cell 142 is suspended in the stack so that the reference gases are heated to substantially the same temperature as the stack gases being measured. This temperature equilibration makes the Doppler broadening for the reference cell gases the same as for the stack gases.

Cell 142 can be filled with a carefully selected combination of gases, such as three or four minority gases in a one atmosphere nitrogen buffer gas. The minority gases can include, for example, hydrogen cyanide, which has a strong absorption line at 14.1 $\mu$m, nitrous acid, which has strong absorption lines at 12.6 and 11.7 $\mu$m, ammonia, with a strong absorption line at 9.1 $\mu$m, and hydrogen chloride, with a strong absorption line at 3.4 $\mu$m. The concentrations of these minority gases can be, for example, 1 to 10 parts per million.

When the AOTF is tuned to an absorbing line of one of the minority species, the difference between the measured stack signal and the reference cell signal is directly proportional to the difference in the concentration-path length products. The absorption lines for the minority species occur at well-known wavelengths and thus the signal from measurement of the reference cell 142 gases provides a dependable means for wavelength calibration of the AOTF, which is an important feature because the tuned wavelength as determined from the acoustic frequency has a second order dependence of the temperature of the AOTF.

When the AOTF is tuned to a wavelength in which the reference cell gases have no absorption, the ratio of the measured stack signal and the measured reference cell signal eliminates any drift which may occur in the baseline of the absorption measurements, significantly improving accuracy.

The AOTF transmits or passes radiation over the entire 1.26 to 16 $\mu$m band. However a single detector cannot efficiently cover this band, and it is preferred to use two or more detectors that are more sensitive at different portions of the band. For example, each of the detectors shown in FIG. 4 can comprise two detectors, such as a HgCdTe detector element for the 5.5 to 14 $\mu$m band and an InSb detector element for the 2.0 to 5.5 $\mu$m band. It is desirable to maintain the same temperature at the detector elements, and therefore all the detector elements preferably are mounted in the same dewar, either side-by-side or in a commercially available sandwich configuration.

In FIG. 4, the second detector 64 measures the total radiation loss through the reference cell, which is a known loss from laboratory measurements, and through the open path stack gases. The total loss measurement is the infrared equivalent of an opacity measurement (which would normally encompass the visible spectrum). Combined with opacity measurements, the total loss measurement via the InSb and HgCdTe elements of detector 64 permits at least an estimate of particle sizes in the stack gas stream, because scattering efficiency is a function of the wavelength to particle diameter ratio.

Meaningful minimum detection levels can be achieved according to the invention to monitor for the heteronuclear polyatomic smoke stack gases listed in the following table, which have the potentially hazardous characteristics shown. These gases have distinct spectra that make them distinguishable in concentrations that are likely to have adverse effects due to short or long term exposure.

TABLE I

| Gas | Formula | Potential Hazard |
| --- | --- | --- |
| Ammonia | $NH_3$ | Flammable |
| Arsine | $AsH_3$ | Toxic, flammable |
| Carbon monoxide | $CO$ | Toxic |
| Ethane | $C_2H_6$ | Flammable |
| Hydrogen chloride | $HCl$ | Corrosive |
| Hydrogen cyanide | $HCN$ | Toxic |
| Hydrogen fluoride | $HF$ | Toxic, corrosive |
| Hydrogen sulfide | $H_2S$ | Toxic, flammable |
| Methane | $CH_4$ | Flammable |
| Nitric oxide | $NO$ | Toxic, oxidizer |
| Nitrogen dioxide | $NO_2$ | Oxidizer, source of smog |
| Ozone | $O_3$ | Oxidizer |
| Pentane | $C_7H_{16}$ | Flammable |
| Phosgene | $COCl_2$ | Toxic |
| Phosphine | $PH_3$ | Toxic, flammable, poison |
| Propane | $C_3H_8$ | Flammable |
| Sulfur dioxide | $SO_2$ | Toxic |

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. An apparatus operable to detect the presence of selected gases in a sample, comprising:
    an infrared source operable to emit an infrared beam along a sight path intersecting the sample, the infrared beam exciting gases in the sample, including at particular excitation wavelengths, thereby causing the gases to emit light at certain emission wavelengths, and to absorb light at certain absorption wavelengths, the emission wavelengths and the absorption wavelengths being characteristic of particular component gases in the sample;
    viewing means directed along the sight path for collecting light from the gases in the sample responsive to the infrared beam;
    an acousto-optical tunable filter coupled to the viewing means, the tunable filter being operable controllably to diffract light collected by the viewing means for selecting particular optical wavelengths and to direct said particular optical wavelengths onto a detector means; and, an analyzer coupled to the detector means and to the tunable filter, the analyzer being operable to control the tunable filter for selecting a plurality of said particular optical wavelengths and to discriminate for presence of said particular component gases by determining a characteristic pattern of the emission and absorption wavelengths detected.

2. The apparatus according to claim 1, wherein the infrared source comprises an infrared laser.

3. The apparatus according to claim 2, wherein the analyzer comprises a processor, and further comprising means coupled to the processor operable to tune the output from the laser to a selected excitation wavelength.

4. The apparatus according to claim 1, wherein the infrared source comprises a broad band infrared source and a collimator.

5. The apparatus according to claim 2, further comprising an output crystal between the laser and the sample, the output crystal producing a harmonic of a wavelength of the laser beam such that the gases are excited at a plurality of wavelengths.

6. The apparatus according to claim 5, further comprising means coupled to the analyzer, for switching the output crystal controllably into and out of the sight path.

7. The apparatus according to claim 6, wherein the analyzer includes a processor operable to control the laser for providing one of a pulsed illumination and a continuous wave illumination along the sight path in an infrared band, the analyzer discriminating for both the absorption wavelengths and the emission wavelengths in the infrared band.

8. The apparatus according to claim 7, further comprising a controllable oscillator controlled by the processor and coupled to the tunable filter for selecting said particular optical wavelengths directed onto the detector means, and wherein the processor is operable to discriminate for a plurality of emission and absorption spectral patterns characteristic of different gases.

9. The apparatus according to claim 8, wherein the acousto-optic tunable filter comprises $Tl_3AsSe_3$.

10. The apparatus according to claim 6, wherein the means for switching the output crystal includes a gimballed mirror.

11. The apparatus according to claim 1, wherein said detector means comprises two detectors and further comprising means for generating simultaneously two orthogonal acoustic waves in the acousto-optical filter at different frequencies, said two detectors receiving light from diffraction at the different frequencies, respectively, such that said two detectors measure two wavelengths at once.

12. The apparatus according to claim 1, further comprising a reference cell containing known gases and means for also directing the infrared beam through the reference cell, the analyzer being operable to compare a response of the sample to a response of the reference cell for at least one of baseline correction and assessment of gas concentrations in the sample.

13. An apparatus operable to detect the presence of selected gases in a sample, comprising:

an infrared source operable to emit an infrared beam along a sight path intersecting the sample, and means for switching the infrared beam between an on-state and an off-state, the infrared beam exciting gases in the sample at particular excitation wavelengths when in the on-state, thereby causing the gases to emit light at certain emission wavelengths, and to absorb light at certain absorption wavelengths, the emission wavelengths and the absorption wavelengths being characteristic of particular component gases in the sample;

viewing means directed along the sight path for collecting light from the gases in the sample responsive to the infrared beam;

an acousto-optical tunable filter coupled to the viewing means, the tunable filter being operable controllably to diffract light collected by the viewing means for selecting particular optical wavelengths and to direct said particular optical wavelengths onto a detector;

an analyzer coupled to the detector and to the tunable filter, the analyzer being operable to control the tunable filter for selecting a plurality of said particular optical wavelengths and to discriminate for presence of said particular component gases by determining a characteristic pattern of the emission and absorption wavelengths detected; and, wherein the analyzer is operable to collect emission wavelengths during the off-state of the infrared source.

14. The apparatus according to claim 13, wherein the infrared source comprises an infrared laser.

15. The apparatus according to claim 14, wherein the analyzer comprises a processor and the infrared laser is switchable under control of the processor.

16. A method for measuring atmospheric gases in a sample, comprising the steps of:

directing an infrared beam through the sample, so as to excite the sample and cause the sample to emit and to absorb light at particular wavelengths that are characteristic of component molecules in the sample;

receiving light from the sample and applying the light to an acousto-optical tunable filter having means for applying an acoustic wave at a predetermined frequency for diffracting the light into a spectrum, and applying the light to a detector means;

varying the predetermined frequency to select among a plurality of wavelengths of absorption and emission at the particular wavelengths that are characteristic of the component molecules;

measuring a level of the light at said particular wavelengths;

analyzing a pattern of the light received from the sample, at the particular wavelengths, for detecting the component molecules in the sample.

17. The method according to claim 16, wherein the infrared beam is obtained from an infrared laser, and further comprising the step of generating harmonics in the laser beam so as to excite the sample at a plurality of wavelengths.

18. The method according to claim 16, wherein the infrared beam is obtained from an infrared laser, and further comprising repetitively selecting for output from the laser a sequence of particular illumination wavelengths of a plurality of wavelengths, and further comprising analyzing successively for particular wavelengths characteristically absorbed by at least one pollutant gas.

19. A method for measuring atmospheric gases in a sample, comprising the steps of:

providing an exciting infrared light beam and means to emit the light beam at selected wavelengths along a beam path intersecting the sample such that the selected wavelengths of the infrared light beam excite component molecules in the sample;

receiving infrared radiation from the sample, the infrared radiation having absorption and emission spectra characteristic of the component molecules;

applying the infrared radiation to an acousto-optical tunable filter and an associated detector means, and tuning the filter by applying to the filter an acoustic wave at an predetermined frequency to diffract the infrared radiation such that a selected wavelength is applied to the detector;

measuring a level of said infrared radiation at the selected wavelength;

tuning the filter by successively applying additional frequencies, measuring the level at the additional selected wavelengths, and proceeding through a set of frequencies sufficient to define the absorption and emission spectra of the sample; and, determining the component molecules of the sample from the absorption and emission spectra.

20. The method according to claim 19, wherein the selected wavelengths are obtained by at least one of tuning a tunable infrared light source, doubling an infrared laser light source and modulating a tunable output crystal inserted along the light beam.

21. The method according to claim 19, further comprising varying an output wavelength of the exciting infrared light beam so as to select an illumination wavelength, tuning the filter and defining the absorption and emission spectra under illumination at a plurality of illumination wavelengths.

22. The method according to claim 21, wherein said detector means comprises two detectors and the method further comprises applying to the filter a second, orthogonal acoustic wave; simultaneously diffracting the infrared radiation along separate paths to the two detectors; and measuring the level at two different selected wavelengths simultaneously.

23. The method according to claim 21, further comprising inserting an output crystal into the beam path and directing the exciting infrared light beam through the output crystal for obtaining a plurality of simultaneous wavelengths of illumination.

* * * * *